(12) United States Patent
Adebayo

(10) Patent No.: US 10,845,322 B2
(45) Date of Patent: Nov. 24, 2020

(54) METHOD AND APPARATUS FOR MEASURING CAPILLARY PRESSURE AND FOAM TRANSPORT IN POROUS MEDIA

(71) Applicant: King Fahd University of Petroleum and Minerals, Dhahran (SA)

(72) Inventor: Abdulrauf Rasheed Adebayo, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 149 days.

(21) Appl. No.: 16/263,149

(22) Filed: Jan. 31, 2019

(65) Prior Publication Data

US 2020/0249182 A1    Aug. 6, 2020

(51) Int. Cl.
*G01N 24/08* (2006.01)
*E21B 49/00* (2006.01)
*G01N 33/24* (2006.01)

(52) U.S. Cl.
CPC ......... *G01N 24/081* (2013.01); *E21B 49/005* (2013.01); *G01N 33/24* (2013.01)

(58) Field of Classification Search
CPC ........ E21B 49/008; E21B 43/26; E21B 47/11; E21B 47/10; E21B 47/00; E21B 49/006;
(Continued)

(56) References Cited

U.S. PATENT DOCUMENTS 2,345,935 A    4/1944  Hassler
3,033,286 A *  5/1962  Fast .................... E21B 49/081
                                                          166/264
(Continued)

FOREIGN PATENT DOCUMENTS

| CN | 203025067 U | 6/2013 |
|---|---|---|
| CN | 102121913 B | 11/2013 |
| WO | 2018/151707 A1 | 8/2018 |

OTHER PUBLICATIONS

Adebayo; Measurements of capillary pressure and relative permeability curves for foam transport in porous media—A capillary bundle approach ; Journal of Petroleum Science and Engineering 172; pp. 1048-1056 ; Sep. 8, 2018; 9 Pages.

(Continued)

*Primary Examiner* — Andre J Allen
(74) *Attorney, Agent, or Firm* — Oblon, McClelland, Maier & Neustadt, L.L.P.

(57) ABSTRACT

A coreflood method that treats a consolidated porous medium, e.g., as a bundle of capillaries of various sizes as a surfactant alternating gas (SAG) method of foam injection. An electrical resistivity tool is used to monitor and measure in-situ changes in water and gas saturation while a high-resolution pressure transducer measures the pressure drop across the sample. A consolidated rock sample pre-saturated with a surfactant solution is injected with a small slug of gas and then a surfactant solution is injected until a steady state flow is observed. Graphical analysis of the saturation and pressure profile in each cycle allows the estimation of water saturation, saturation of the mobile and trapped fractions, and a corresponding pressure drop. Similarly, graphical analysis of the saturation and pressure profile in multiple SAG cycles generates a data set as a function of pore size, water saturation, and capillary pressure. The data are used for a variety of foam analyses to generate a capillary pressure curve for foam transport in a porous medium, to generate initial-residual (IR) gas saturation curve, estimation of gas trapping coefficient, estimation of limiting capillary pressure, critical water saturation, and/or other foam flow characterization.

8 Claims, 5 Drawing Sheets

(58) Field of Classification Search
CPC .......... E21B 43/16; E21B 49/10; E21B 43/25;
E21B 49/08; E21B 49/00; E21B 43/20;
E21B 47/06; E21B 49/081; E21B 21/08;
E21B 33/124; E21B 33/1243; E21B
43/12; E21B 43/24; E21B 47/07; E21B
47/135; E21B 49/082; E21B 47/017;
E21B 47/107; E21B 47/113; E21B 49/02;
E21B 23/03; E21B 33/068; E21B
33/1275; E21B 33/138; E21B 37/06;
E21B 41/0035; E21B 41/02; E21B
43/122; E21B 43/123; E21B 43/2406;
E21B 47/01; E21B 47/117; E21B 49/005;
E21B 49/087; E21B 49/088; E21B
17/203; E21B 17/206; E21B 21/00; E21B
21/002; E21B 21/003; E21B 21/062;
E21B 21/065; E21B 23/08; E21B 25/00;
E21B 25/08; E21B 33/072; E21B 33/13;
E21B 34/06; E21B 34/066; E21B 34/08;
E21B 34/16; E21B 36/001; E21B
41/0057; E21B 41/0064; E21B 41/0099;
E21B 43/00; E21B 43/261; E21B 43/267;
E21B 47/002; E21B 47/005; E21B 47/09;
E21B 47/103; E21B 47/12; E21B 49/06;
G01N 33/2823; G01N 33/24; G01N
21/31; G01N 33/241; G01N 11/08; G01N
11/14; G01N 15/02; G01N 15/088; G01N
2015/0053; G01N 21/64; G01N 25/66;
G01N 33/28; G01N 9/36
USPC .............. 73/152.05, 152.11, 152.22, 152.41,
73/152.51, 152.39
See application file for complete search history.

(56) References Cited

U.S. PATENT DOCUMENTS

| 5,297,420 | A | 3/1994 | Gilliland et al. | |
|---|---|---|---|---|
| 10,669,818 | B2* | 6/2020 | Bourbiaux | E21B 49/00 |
| 2013/0091941 | A1* | 4/2013 | Huh | E21B 49/008 |
| | | | | 73/152.08 |
| 2014/0274817 | A1* | 9/2014 | Hill | C09K 8/602 |
| | | | | 507/211 |
| 2016/0195465 | A1* | 7/2016 | Mikhailov | E21B 49/00 |
| | | | | 73/152.05 |
| 2017/0248506 | A1 | 8/2017 | Gupta et al. | |
| 2018/0171788 | A1* | 6/2018 | Waid | E21B 49/088 |
| 2019/0330959 | A1* | 10/2019 | Dogru | E21B 47/06 |
| 2020/0049002 | A1* | 2/2020 | Nakutnyy | G01N 33/24 |

OTHER PUBLICATIONS

Adebayo, et al.; Exploring a mechanistic approach for characterizing transient and steady state foam flow in porous media; Journal of Natural Gas Science and Engineering 60; pp. 214-227; Oct. 26, 2018; 14 Pages.

Adebayo; Viability of foam to enhance capillary trapping of CO2 in saline aquifers—An experimental investigation; International Journal of Greenhouse Gas Control 78 ; pp. 117-124; Aug. 20, 2018; 8 Pages.

Aronson, et al.; The influence of disjoining pressure on foam stability and flow in porous media; Colloids and Surfaces A: Physicochemical and Engineering Aspects 83; pp. 109-120; Aug. 5, 1993; 12 Pages.

Khristov, et al.; Influence of the pressure in the Plateau-Gibbs borders on the drainage and the foam stability; Colloid & polymer Sci. 257; pp. 506-511; Feb. 1, 1978; 6 Pages.

Kibodeaux, et al.; Coreflood Study of Surfactant-Alternating-Gas Foam Processes: Implications for Field Design; Society of Petroleum Engineers, Inc.; pp. 567-577; 11 Pages.

Khatib, et al.; Effects of Capillary Pressure on Coalescence and Phase Mobilities in Foams Flowing Through Porous Media; Society of Petroleum Engineers; SPE Reservoir Engineering ; Aug. 1988; 8 Pages.

* cited by examiner

METHOD AND APPARATUS FOR MEASURING CAPILLARY PRESSURE AND FOAM TRANSPORT IN POROUS MEDIA

STATEMENT OF ACKNOWLEDGEMENT

The inventor acknowledges the support provided by the College of Petroleum Engineering and Geosciences at King Fahd University of Petroleum & Minerals (KFUPM) for funding this work.

STATEMENT OF PRIOR DISCLOSURE BY THE INVENTOR

The inventor disclosed capillary pressure and relative permeability methods in "Measurements of capillary pressure and relative permeability curves for foam transport in porous media-A capillary bundle approach" which published online on Sep. 18, 2018 in the *Journal of Petroleum Science and Engineering*, Volume 172, pages 1048-1056, and an analysis of steady state foam flow in "Exploring a mechanistic approach for characterizing transient and steady state foam flow in porous media" which published online on Oct. 26, 2018 in the *Journal of Natural Gas Science and Engineering*, Volume 60, pages 214-227, and "Viability of foam to enhance capillary trapping of $CO_2$ in saline aquifers—An experimental investigation" which was published online on 20 Aug. 2018 in the *International Journal of Greenhouse Gas Control*, Volume 78, pages 117-124, all of which are incorporated herein by reference in their entireties.

SUMMARY OF THE INVENTION

Field of the Invention

This invention relates to coreflood testing methods and apparatuses. In particular, this invention relates to coreflood methods and apparatuses used to measure capillary pressure curves and initial-residual gas saturation curves used in methods for characterizing porous media and foam transport therein.

Discussion of Related Art

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly or impliedly admitted as prior art against the present invention.

Relative permeability, capillary pressure, and wettability are key physical properties of the underground area or well media that are typically determined in oil reservoir discovery. These characteristics/properties are used to determine, inter alia, the type of injection fluids that may be used for well treatment. In order to determine these properties core samples are removed from identified underground structures and are tested for aforesaid key physical properties.

Foam is used in a variety of applications such as enhanced oil recovery (EOR) processes. Foam injection in reservoir rocks is an effective method used during oil recovery. Foam mobility in a porous medium is governed mainly by the properties of the foam and the capillary pressures in the porous medium. However, the bubbles of any type of foam will rupture or coalesce when the capillary pressure occurring during flow in a porous medium reaches a maximum value called the limiting capillary pressure (Pc*).

Foam is a fluid that includes a gas phase dispersed in a liquid phase separated by lamellae, and can be injected into a porous media in different ways. A foaming agent such as surfactant facilitates the formation and sustenance of the foam bubbles. Foam models and parameters are often derived from laboratory coreflood data determined at a steady state foam flow regime, which makes them unsuitable or inaccurate for simulating transient foam flow. Since significant foam trapping occurs in the transient flow regime, foam trapping processes are not adequately covered by existing models.

Khatib et al. ("Effects of capillary pressure on coalescence and phase mobilities in foams flowing through porous media," *Soc. Pctr, Eng. Res, Eng.* 3 (3), 919-926 1988.—incorporated herein by reference in its entirety) and Aronson et al. ("The influence of disjoining pressure on foam stability and flow in porous media," *Colloid. Surface. Physicochem. Eng. Aspect.,* 83 (2), 109-120. https://doi.org/10.1016/0927-7757(94)80094-4—incorporated herein by reference in its entirety) measured the individual pressure of gas and liquid phases during steady state foam flow in sand packs (with permeability in the range of 2-270 Darcy) using pressure probes placed inside the sand pack. The pressure difference between the gas phase and the liquid phase (surfactant) at steady state represented the limiting capillary pressure (Pc*=$P_{nw}$-$P_w$). However, it was not possible to measure the capillary pressures before steady state foam flow (or before Pc*). Kibodeaux and Rossen ("Core Flood Study of Surfactant-alternating-Gas Foam Processes: Implications for Field Design," *Society of Petroleum Engineers,* https://doi.org/10.2118/38318-MS—incorporated herein by reference in its entirety) reported a similar but indirect method for determining pressure differences in consolidated rock by incorporating a semipermeable ceramic disc to measure the pressure of the wetting phase. Other researchers (e.g. Mysels, 1964; Khristov et. al., 1979; Khristov et al., 1983; and Aronson et al., 1994—"Soap films and some problems in surface and colloid chemistry 1," *J. Phys. Chem.* 68 (12), 3441-3448, https://doi.org/10.1021/j100794a001; *Colloid Polym. Sci.* 261 (3), 265-270. https://doi.org/10.1007/BF01469674; "Influence of the pressure in the Plateau-Gibbs borders on the drainage and the foam stability. Colloid Polym. Sci. 257 (5), 506-511. https://doi.org/10.1007/BF01626229—each incorporated herein by reference in its entirety) reported a method that involves the use of a high resolution light microscope to measure the thickness of foam film present on a porous plate at different capillary pressures until foam rupture. The limiting capillary pressure at which the film ruptured was also termed the disjoining pressure. None of these methods could be conducted directly in a consolidated porous medium. Furthermore, only one point of capillary pressure was measured, e.g., at a steady state or at foam rupture.

US published application 2017/0248506 A1 (to Gupta et al.) used a dual injection method (simultaneous injection of gas and liquid), to determine relative permeability and capillary pressure of a core sample from the measurements obtained from a single core flood test, and a capillary pressure curve from the capillary pressures determined from each set of steps. Gupta, however, did not use surfactants with colloids, and used a plurality of measurements by using dual pumps (dual injection) at different fluid ratios to force variation in water saturation at different fluid ratios, and used the steady state pressure drop and water saturation at each fluid ratio to generate the capillary pressure curves.

U.S. Pat. No. 2,345,935 to Hassler (Apr. 4, 1944) used a method for determining the permeability of a porous body to fluid flow. The method included obtaining values of capillary pressure for different flow rates and degrees of saturation. The values were further used to draw curves for capillary pressure against saturation. However, it was not possible to obtain separate measurements for injected and corresponding trapped gas at each stepwise change in water saturation nor was it possible to measure foam flow behavior in porous media.

WO 2018/151707 A1 describes a three-dimensional reservoir simulator used for automated upscaling relative permeability and capillary pressure in multi-porosity systems comprising disparate rock-types. A coarse-scale single-porosity model incorporating multi-porosity model properties may be derived from a fine-scale single-porosity model based, at least in part, on simulation of a model comprising data from one or more regions of interest. Real-world and laboratory measurements of the one or more regions of interest may be provided to the fine-scale single-porosity simulation model and the fine-scale single-porosity model may be subjected to one or more fractional flow simulation processes and one or more displacement simulation processes. Capillary pressure is computed by simulating a hydrostatic pressure rise in an oil-water system through different heights of a hypothetical rock system. A plurality of capillary pressures and water saturations were determined by ascribing different porosity values (or different petrophysical properties) to different segments (e.g. bottom to top) of the rock system. This invention, however, did not use surfactants with colloids.

U.S. Pat. No. 5,297,420 to Gilliland et al. (Mar. 29, 1994) describes an apparatus and method for measuring relative permeability and capillary pressure of porous rock. A semi permeable membrane that is selectively permeable to the wetting phase, and another permeable membrane permeable to both wetting and non-wetting phases were used to measure rock capillary pressure and relative permeability at different saturation levels. The injection strategy included pre-mixing the two phase (gas/water) system before injection into a rock sample and separately producing the two phases at the sample outlet. The process is repeated at different gas/water ratios. A steady state pressure drop and saturation during each ratio is used to generate the capillary pressure curve. This strategy does not use foams and a cyclic injection method to measure capillary pressure and relative permeability. In addition, it cannot be used to characterize the flow behavior of the foam in the porous medium. Chinese Pat. No. CN 203025067 B to Sinopec Corporation discloses a low-osmosis rock sample permeability tester that measures only permeability, and uses only a gas phase. A method to measures gas permeability in tight rock samples was disclosed, however, a method of measuring capillary pressure and relative permeability (using foam) was not disclosed.

Chinese Pat. No. CN 102121913 B (Nov. 27, 2013) discloses a detection method for foam stability in porous medium and a device therefor that uses electrical resistance measurements to estimate a foam stability factor. The result gives a quantitative and dimensionless value as a function of time. However, the method uses a porous medium simulator, not a single coreflood experiment in combination with capillary pressure and other measured data points to characterize foam transport in porous media.

The use of colloids to generate capillary pressure, relative permeability, and I-R (initial-residual gas saturation) curves of consolidated and/or unconsolidated porous materials as a basis for (i) evaluating and screening the effectiveness of the colloids with respect to their strength, stability, and (ii) evaluating rock properties and flow behavior in underground reservoir rocks and at the reservoir conditions has not been disclosed.

Accordingly, it is one objective of the present disclosure to describe an apparatus and method to measure capillary pressure values (e.g., continuous) at different water saturation values and in consolidated rocks at various reservoir conditions, by systematic injection and sequential trapping of foam bubbles in different pore sizes (or capillary pressures), to thereby generate I-R and capillary pressure curves that are used as behavioral or performance indicators for foam transport in porous media. In one aspect, multiple foam parameters are measured from a single core flooding experiment.

SUMMARY OF THE INVENTION

In one aspect the present disclosure provides a method for determining capillary pressure, relative permeability, and/or initial-residual (IR) gas saturation curves for a porous rock sample In another aspect the method includes saturating the rock sample with a surfactant solution to form a saturated rock sample then treating the rock sample to a plurality of injection cycles.

In another aspect the method includes a first injection cycle including injecting a first volume of a gas into the saturated rock sample at a first injection rate, wherein the first volume of the gas is from 0.01 to 0.5 the pore volume of the rock sample; then injecting the surfactant solution at the first injection rate into the saturated rock sample and continually measuring at least one or both of the electrical resistivity or the pressure drop across the rock sample, wherein the surfactant solution is injected until at least one or both of the electrical resistivity and the pressure drop maintain a constant value.

In another aspect the method includes further includes one or more further injection cycles including injecting a second volume of a gas into the saturated rock sample at the first injection rate, wherein the second volume of the gas is from 0.01 to 0.5 the pore volume of the rock sample; then injecting the surfactant solution at the first injection rate into the saturated rock sample and continually measuring at least one of the electrical resistivity or the pressure drop across the rock sample, wherein the surfactant solution is injected until at least one of the electrical resistivity and the pressure drop maintain a constant value.

In another aspect the method includes continuing the further injection cycles until at least one of the electrical resistivity or the pressure drop across the rock sample after an injection cycle is the same as the electrical resistivity or the pressure drop across the rock sample of a preceding injection cycle; determine at least one of a capillary pressure curve and a water saturation curve based on the plurality of constant values of electrical resistivity and/or pressure drop from the injection cycles.

In another aspect the method the injection cycles are carried out in a single coreflood of the rock sample.

In another aspect the method the pressure drop is measured with a high resolution pressure transducers; and the electrical resistance is measured with an LCR meter.

In another aspect the method further includes estimating a foam stability in the rock sample.

In another aspect the method the foam stability is at the foam rupture point of the surfactant solution.

In another aspect the surfactant solution further comprises one or more nanoparticles.

In another aspect the surfactant solution comprises polymer nanoparticles.

In still a further aspect the present disclosure provides a coreflooding apparatus for measuring at least one of capillary pressure and initial-residual (IR) gas saturation of a porous media.

In still another aspect the coreflooding apparatus includes a hydrostatic core holder, having an inlet port and an outlet port.

In still another aspect the coreflooding apparatus includes two floating-piston fluid cylinders, wherein one of said floating-piston fluid cylinders contains a surfactant solution while the other floating-piston fluid cylinders contains a gas, and wherein the hydrostatic core holder and said two floating-piston fluid cylinders are disposed either inside or outside an oven.

In still another aspect, in the coreflooding apparatus the inlet port is configured to allow fluids to be injected into one end of a rock sample and to be produced at the outlet port at an opposite end of the rock sample.

In still another aspect, in the coreflooding apparatus the inlet and outlet ports are connected to pressure transducers, configured to measure a pressure drop across the rock sample.

In still another aspect the coreflooding apparatus includes an injection pump to displace the fluid from the floating piston cylinders at a constant injection rate.

In still another aspect the coreflooding apparatus includes a gas dome backpressure regulator configured to provide a back pressure to the rock sample.

In still another aspect the coreflooding apparatus includes one or more electrode rings imbedded inside a rubber sleeve configured to hold the rock sample in the hydrostatic core holder.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
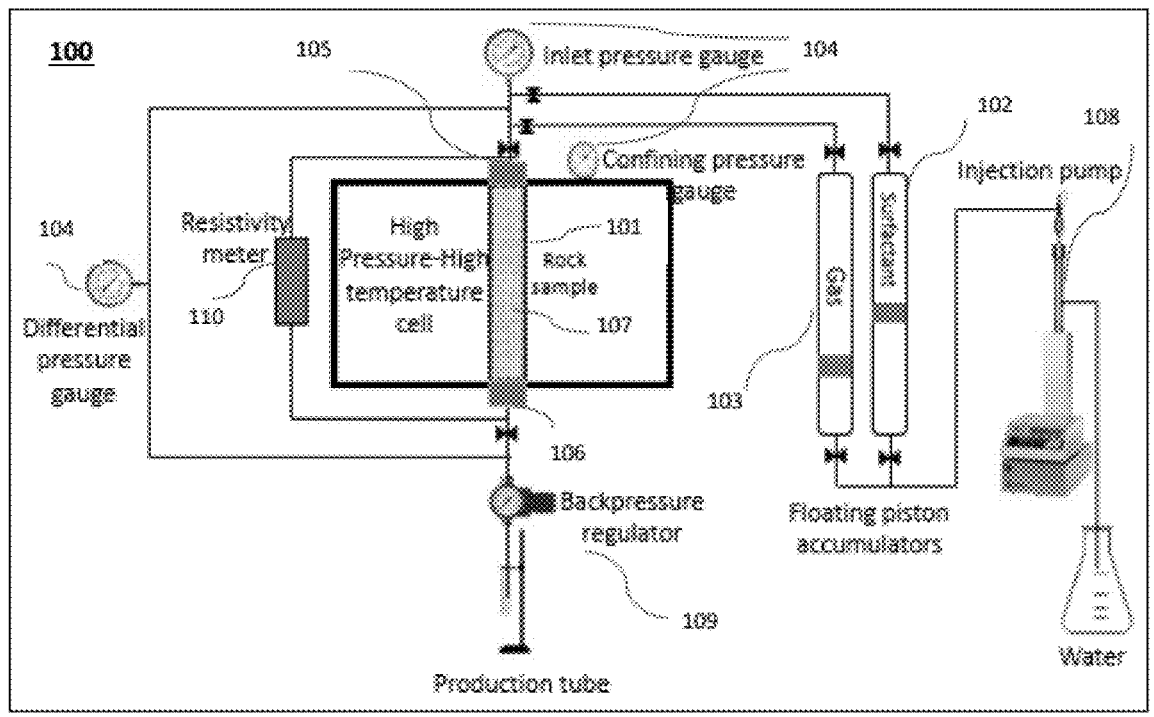
FIG. 1 shows the setup of a core flooding apparatus according to the present invention.

Aspects of the present invention will be described hereinbelow in conjunction with the above-described drawings.

The present disclosure includes a foam characterization method, system and apparatus for measuring and/or determining multiple foam parameters from a single core flooding experiment. In other aspects the present disclosure describes enhancments of foam flow modeling in both the transient and steady state foam flow regime. The ability to directly measure these parameters relating to foam flow in a single core flooding experiment allows for limiting the number of model parameters to be fine-tuned when history matching simulation results with laboratory and/or in situ data. It also permits the use of constraints (e.g., upper and/or lower allowable limits) to be imposed for some model parameters during data fitting, hence, improving confidence, accuracy and fit to field conditions.

The method of the present disclosure permits measurement of the capillary pressure curve and initial-residual (I-R) gas saturation curve during foam flow in a single core flood experiment. Since the behavior of the capillary pressure and I-R curves depend on the properties of the foam and porous medium, the two curves can be used as behavioral and/or performance indicators for foam transport in porous media. Embodiments of the present invention include methods, systems and apparatuses for the following:

1. Measuring capillary pressure and I-R (initial-residual gas saturation) properties and curves of consolidated and/or unconsolidated porous materials with colloids (e.g., compositions such as surfactant foams optionally containing nanoparticles, polymers, etc.).
2. Methods for evaluating and/or screening colloids with respect to their strength, stability, gas trapping coefficient, and flow behavior in underground reservoir rocks and at the reservoir conditions according to their respective capillary pressure and I-R curves.
3. Methods for concurrently or separately measuring (i) rock-fluid properties and (ii) properties of colloids in rock.
4. Methods that accomplish each of (1)-(3) in a single coreflood experiment.

In contrast to conventional techniques the methods, systems and apparatuses of the present disclosure (i) use colloids (e.g., surfactant foam compositions that optionally contain nanoparticles or other additives/stabilizing agents), and (ii) utilize different techniques for fluid injection (e.g., cyclic injection and/or alternate injection).

In various embodiments of the present invention, continuous capillary pressure values are measured at different water saturation conditions and/or in consolidated rock at reservoir conditions, by a systematic injection and sequential trapping of foam bubbles in different pore sizes (or capillary pressures). The steady state pressure drop at each sequence of gas trapping is related to the capillary pressure at such trapped gas saturation (or equivalent water saturation). This allows an IR curve to be generated. The maximum capillary pressure in the capillary pressure curve and the corresponding water saturation represent the limiting capillary pressure and critical water saturation of the foam respectively. Since the behavior of the capillary pressure and I-R curves depend on the properties of the foam and porous medium, the two curves can be used as a basis for determining the behavioral and/or performance characteristics of foam transport in porous media.

Figure 2:
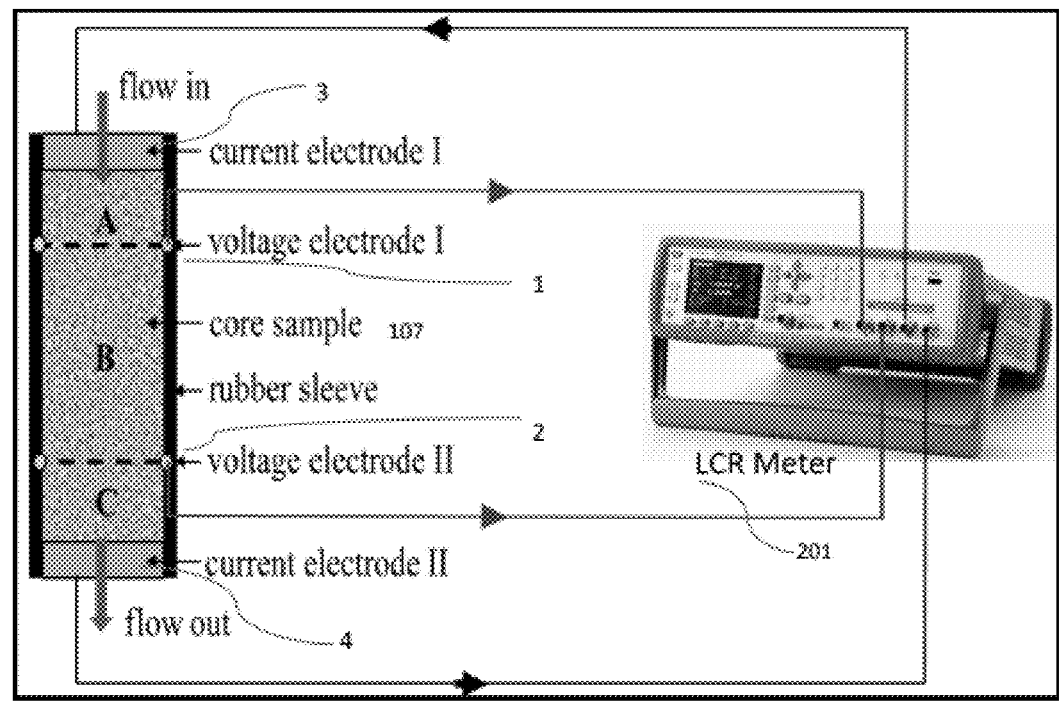
FIG. 2 illustrates the electrical resistivity measurement configuration for the core holder shown in FIG. 1.

According to one embodiment of the invention, the core flooding apparatus 100 shown in FIG. 1 is used. The core flooding apparatus includes a hydrostatic sample holder rated for a confining pressure, e.g., of up to 10,000 psi and temperature, e.g., of up to 150° C.; preferably pressures of 1,000-10,000, 2,000-8,000, 3,000-7,000 or about 5,000 psi and temperature from 25 to 250° C., 50 to 200° C., or 100-150° C. An electrical resistivity probe and a high resolution pressure transducer are attached to the core holder to transmit real time and in-situ data to a nearby computer. A syringe pump and one or more fluid accumulators are used to control injection into rock samples. Another syringe pump (not shown) may optionally be used to supply a constant confining pressure to the core holder More specifically, the setup of the core flooding apparatus 100 includes a hydrostatic core holder 101 and two floating-piston fluid cylinders 102 and 103, all mounted inside a large oven. One of the cylinders 102 contains the surfactant solution while the other 103 contains the gas. The core holder 101 has inlet and outlet ports 105 and 106. The inlet port 105 allows fluids to be injected into one end of a rock sample 107 placed and to be produced at the outlet port at the other end of the sample 107. The inlet and outlet ports are also connected to a set of high-resolution pressure transducers 104, which measure the pressure drop across the sample 107. An injection pump 108 is used to displace the fluid (gas or liquid) from the floating piston cylinder at a constant injection rate of 0.5 cm³/min into the rock sample 107 via high pressure steel tubes. Another pump provides a constant confining pressure, e.g., of 2200 psi, to the core holder. A gas dome backpressure regulator 109 provides a back pressure, e.g., of 1450 psi, to the sample. Automatic valves are preferably installed at the upstream of the core holder 101 and floating piston accumulators 102 and 103, and are used to remotely control fluid flow through the rock sample 107 without having to open the oven. Electrode rings (see FIG. 2) are imbedded inside the rubber sleeve that houses the rock sample 107 in the core holder 101. Four long conductive wires are passed through the core holder to connect the electrode rings to a LCR meter 201 (as shown in FIG. 2). The LCR meter 201 transmits electric current (electrode 3 and electrode 4) through the rock sample 101 while the voltage electrode rings (electrode 1 and electrode 2) measure the voltage drop and electric resistance between them during the coreflooding process.

Another embodiment of the present invention includes a method for coreflood analysis to measure foam transport properties, a single experiment, using the core flooding apparatus described above. These coreflooding procedures are now disclosed hereinbelow for an example case.

EXAMPLE

A test sample of cylindrical rock (10.6 cm long and 3.76 cm in diameter) was extracted from an Indiana limestone outcrop (with porosity of 15% and brine permeability of 5 mD). The sample was cleaned by flushing with methanol in a Soxhlet apparatus at 80° C. for three days in order to remove any salt deposits that may be in its pores. It was then dried in a vacuum oven for 24 hours in order to dry and evacuate the pores. The sample was then saturated with a brine solution containing dissolved surfactant. Saturation was conducted by vacuum method after which the sample porosity and pore volume were estimated based on the difference of it's dry and saturated weights. Synthetic brine solution of 58,000 ppm was formulated in the lab using salt compositions similar to those found in typical reservoir water. A surfactant solution containing 0.025% weight concentration of surfactant dissolved in brine was also prepared. The surfactant used is a non-ionic ethoxylated fluorocarbon surfactant containing 40% active contents. The surfactant concentration in brine was above its critical micelle concentration. Other types of surfactant or foaming agents can be used. A high purity (99.9%) nitrogen gas was used as the gas phase. Crude oil was not included at this stage.

The test sample, which was pre-saturated with surfactant solution, was placed in the core holder 101 of the Core flooding apparatus 10, and then gradually subjected to both a confining pressure of 2200 psi and a pore pressures (or backpressure) of 1450 psi using two different syringe (Isco) pumps. The pore pressure and back pressure were both increased stepwise such that the difference between the confining pressure and pore pressure at any time was 750 psi. The oven temperature was also gradually raised to the required temperature of 45° C. Prior to the start of experiments, the sample was continuously circulated with surfactant solution under a constant back pressure of 1450 psi and at a rate of 0.05 cm³/min for over 24 hours to allow all surfactant adsorption to take place in the pores of the samples and also to expel any trapped gas.

Figure 3:
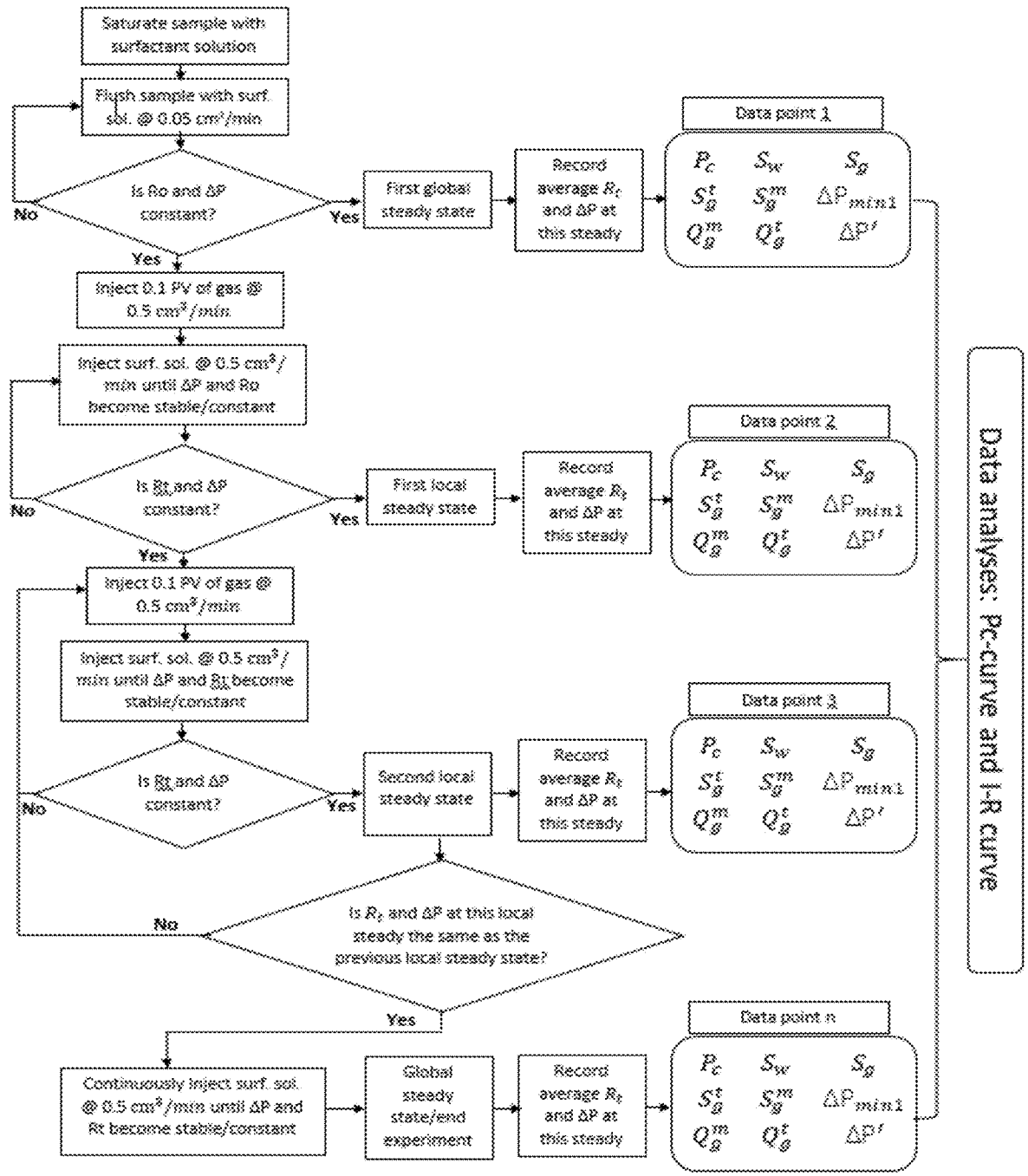
FIG. 3 illustrates the experiment process chart for enforcing plurality of capillary pressure and water saturation

A systematic and cyclic injection of gas and surfactant at a constant injection rate then followed according to the process flow diagram shown in FIG. 3. Each cycle involves injecting 0.1 pore volume (PV) of gas at a constant rate of 0.5 cm³/min followed with a continuous injection of surfactant at the same injection rate until a steady state surfactant injection is attained. A steady state is adjudged to be attained when the electrical resistivity and pressure drop measurements maintain a constant value over a sufficient period of time. An automatic (pneumatic) valve was used to switch between gas and surfactant injection. After a steady state surfactant injection, another cycle started immediately by injecting another slug of gas followed by surfactant injection until a new steady state surfactant flow was attained. The cyclic process was repeated for multiple cycles. The experiment was ended when the resistivity and pressure drop values at a steady state in a given cycle is the same as the values in the steady state of the cycle preceding it. This means that for each cycle, a steady state will be attained. This steady state is termed a 'local steady state' while the final steady state is termed a 'global steady state'. A global steady state is reached when two local steady state resistivity and pressure drop values are equal. Pressure data (using high resolution pressure transducer) and electrical resistance (using LCR meter) across the sample are collected during experiments and transmitted to a nearby computer. The resistance values are then later used to estimate water saturation based on Archie (1942) equation. The calibration of resistivity measurements and conversion to water saturation was reported in a previous study (Adebayo et. al., "An investigation of the effect of CO2-brine-rock interaction on determination of Archie's saturation exponent for carbon dioxide evaluation in carbonate reservoirs," *Journal of Petroleum Science and Engineering*, 133, 665-676, https:// doi.org/10.1016/j.petrol.2015.05.005, incorporated herein by reference in its entirety). Crude oil was not used in this example. The measured data are shown graphically in FIG. 4.

The amount of gas injected for each cycle of injecting is preferably from 0.01 to 0.5× the pores volume of the rock sample, preferably from 0.05 to 0.4, 0.1 to 0.3 or about 0.2× pore volumes of the rock sample. The pore volume is preferably measured using a device such as a Boyles' porosimeter. Other methods of determining the pore volume of the rock sample include mercury/fluid injection methods such as the Wash-Bunting, Kobe or similar methods, and/or fluid saturation methods that determine the amount of fluid volume held by a particular rock sample. The total porosity of the rock sample is the fraction of a total rock volume that is not occupied by solid matter. Porosity may include pores of different volume, different degrees of connectivity and different pore size. Displacement methods such as the Archimedes method determine the pore fraction by fluid displacement in the bulk volume of the rock sample to provide a measure of connected porosity. This is the preferable porosity used for determining the volume of gas for injection into the gas sample. A bulk volume measurement of a rock sample is typically obtained by physical measurements of the rock sample.

The gas and surfactant solution are preferably injected into the rock sample at a constant rate. Preferably the rate of fluid injection (gas and surfactant solution) is the same for both steps of injecting. Preferably the constant rate of injection is from 0.01 to 5.0 cm³/min, preferably 0.05 to 1 cm³/min, 0.1 to 0.8 cm³/min, or 0.3 to 0.6 cm³/min or about 0.5 cm³/min.

Steady-state for particular cycle of injection is reached when measurements of one or more of electrical resistance and pressure drop do not change by more than 5%, 1%, 0.5%, or 0.1% between measurements. Preferably, the measurements are taken at a frequency of at least one per minute, at least 10 per minute, or at least 60 per minute. Steady state is reached between alternating injection cycles when at least one of the values of electrical resistance and pressure drop to not change by more than 10%, 5%, or 1% between measurements of a present and preceding injection cycle. There is no limit to the number of injections cycles that may be carried out before a steady-state between injection cycles is reached. Preferably the number of injection cycles ranges from 2 to 100, 5 to 150, 10 to 100, or about 50 cycles.

Electrical resistivity measurements are converted to water saturation using the Archie equation (Archie, G. E., "The electrical resistivity log as an aid in determining some reservoir characteristics," Trans. of AIME, 1942 146 (1), 54-62, https://doi.org/10.2118/942054-G—incorporated herein by reference in its entirety), which relates electrical resistivity measurements in a porous medium to its water saturation as shown in equation (1). The uncertainty in the saturation and pressure measurements reported below are ±0.02 and ±0.1 psi respectively.

$$S_w = \left(\frac{R_o}{R_t}\right)^{\frac{1}{n}} \quad (1)$$

Where $S_w$ is the water saturation, $R_o$ is the electrical resistivity of the rock when it is saturated with water, $R_t$ is its electrical resistivity when it is partially saturated with water, n is the saturation exponent of the rock. The saturation exponent, 'n' was experimentally derived from multiple measurements with a value of 1.18±0.02. Details of the procedure are given in a previous study (Adebayo et al., 2015—incorporated herein by reference in its entirety). Since only two phases exist during coreflooding, the gas saturation was estimated as, $S_g=1-S_w$.

Figure 6:
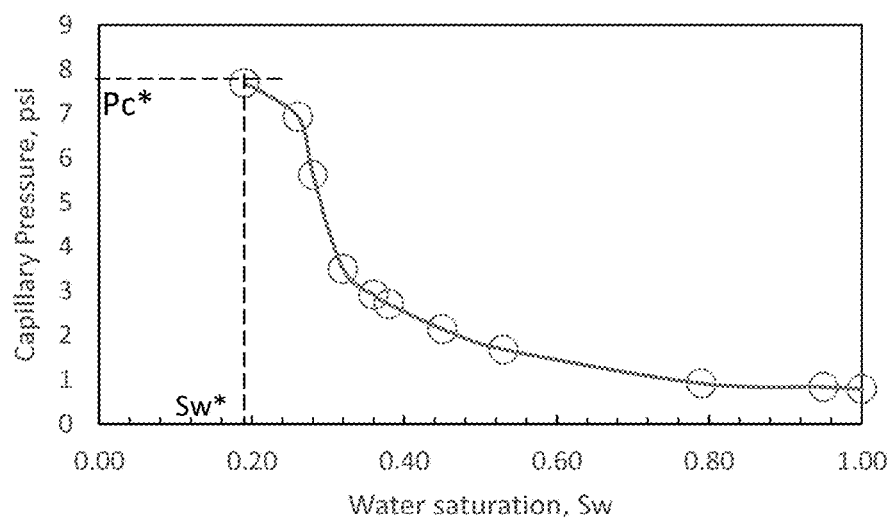
FIG. 6 shows the capillary pressure curve characterizing foam flow plotted by using some of the measured data set in accordance with the present invention.
Figure 7:
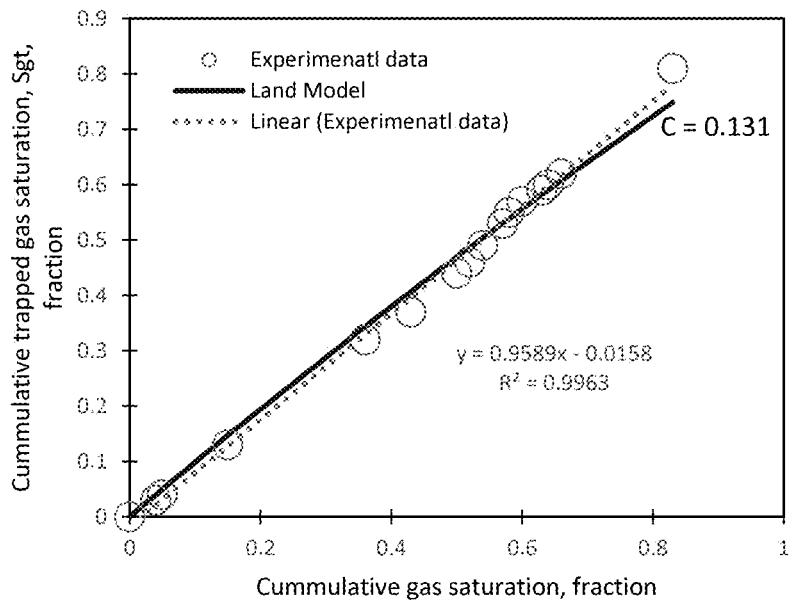
FIG. 7 shows the Initial-Residual saturation curve characterizing foam flow plotted by using some of the measured data set in accordance with the present invention.

A graphical analysis of the measured saturation and pressure data is shown graphically in FIGS. 6 and 7. The in-situ water saturation in each sample is 100% ($S_w=1$) prior to gas injection. During the injection of the first gas slug in the first cycle, foam bubbles were generated that displace a fraction of the surfactant solution initially in the pores of the rock sample. The generated foams at this stage impose only a limited capillary pressure and thus penetrate only the big set of pores and throats with the lowest capillary entry pressures (shown as capillary bundle size #1). The water saturation profile declines during gas injection until the injection is switched from gas to surfactant. The injected surfactant solution displaces a fraction of these foam bubbles (i.e. the mobile gas bubbles) from the sample and sweeps it to the sample outlet. Hence, the rise again in the water saturation profile. A fraction of the foams that cannot be swept during surfactant injection is thus the trapped gas bubbles in this bundle of capillaries (capillary bundle size #1). At a steady state flow of the surfactant in this cycle, all the mobile gas bubbles, have already been displaced resulting in a constant water saturation profile, Sw1, shown in the figures. This steady state is thus the first local steady state.

In the second cycle, more gas is injected to generate more foams (gas bubbles). At this stage, the flow channel of the new gas bubbles is restricted to pore sizes (higher capillary pressure, Pc2-pores) smaller than those initially occupied by trapped gas bubbles in the previous cycle (low capillary pressure, Pc$_1$-pores). The surfactant injection that follows the gas injection in this cycle also sweeps a fraction of the newly generated foam (the mobile gas bubbles) across the sample while a fraction is also trapped in this new set of pores and throats. Hence, a second local steady state is attained at Sw2. Consequently, the cumulative trapped gas in the sample is also increased. Capillary bundle size #2 (shown in cycle 2) thus represents the combination of the capillaries in cycle 1 and cycle 2 whose cumulative volume and capillary pressure, equal the volume of the cumulative trapped gas and the new local steady state pressure drop respectively.

Figure 4:
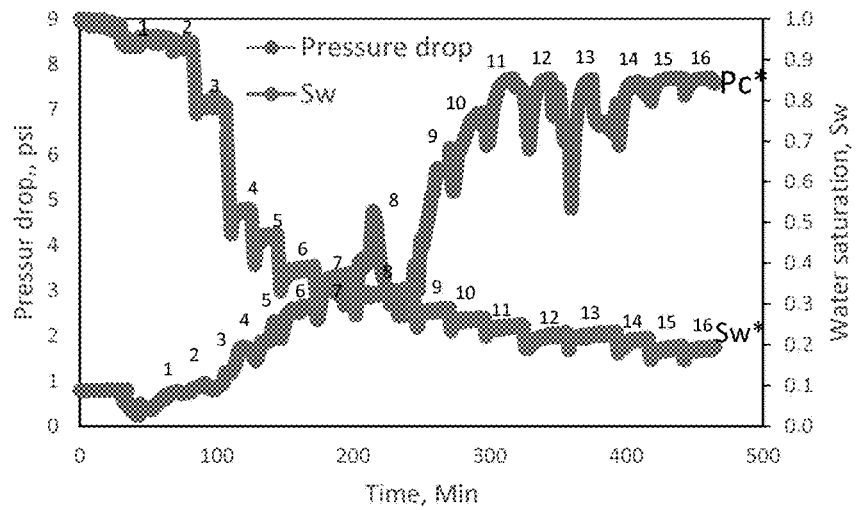
FIG. 4 illustrates the simultaneous and real time measurements of pressure and in situ water saturation during surfactant alternating gas injection in accordance with the present invention.

The cyclic injection process is repeated many times allowing more and smaller pores (higher capillary pressure pores) to be penetrated by the foam. Thus, each successive cycle represents the cumulative trapping of gas bubbles in a specific size range of capillaries present in the sample. However, not all the capillary sizes (or capillary pressure) present in the samples can be penetrated by the foam bubbles. Khatib et al. (1988) identified a limiting capillary pressure value, Pc*, above which foams collapse during flow in a porous medium. This maximum capillary pressure is a function of the surfactant used to generate the foam, the salinity of the brine, the temperature of the porous medium, and the injection rates. The stronger a gas bubble, the higher the pressure it can withstand before rupturing. The maximum pressure a foam bubble can withstand before rupturing was earlier discovered to be the disjoining or rupture pressure of the foam (Khristov et al., 1979). Khatib et al. (1988) reported that at Pc*, the disjoining pressure of the foam is reached and the foam bubbles coalesce at this value to keep the capillary pressure from rising above the Pc* value. In other words, the capillary pressure and water saturation remain constant at Pc*(Sw*). In the saturation and pressure profiles shown in FIG. 4, the injection cycle is stopped when it is obvious that the gas bubbles could not penetrate smaller capillaries. The local steady state in cycle 15 and cycle 16 remain the same. In other words, a global steady state is attained and the water saturation, Sw (or trapped gas saturation) remains constant. As shown in the figure, $Sw_{15}=Sw_{16}$ and $Pc_{15}=Pc_{16}$ (where the subscripts refer to the injection cycle). Hence, the Pc*(Sw*) value is attained at the $15^{th}$ cycle as shown in FIG. 4.

Figure 5A:
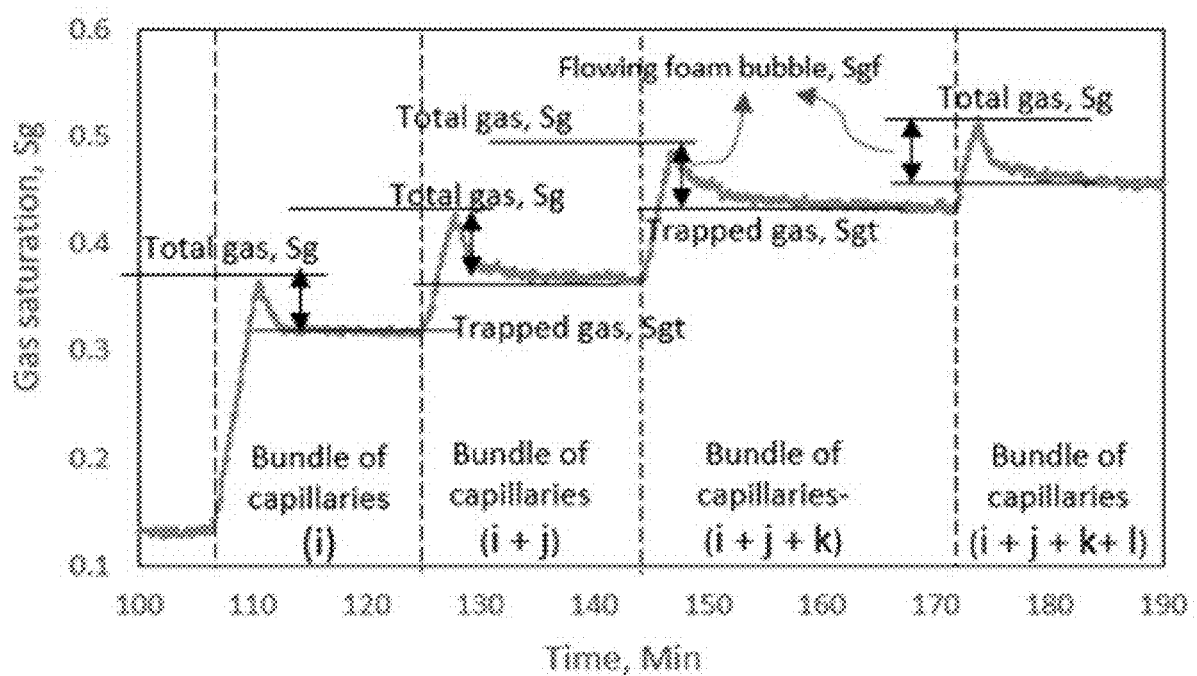
FIG. 5A is a graphical illustration of foam trapping process in a porous medium in accordance with the present invention.
Figure 5B:
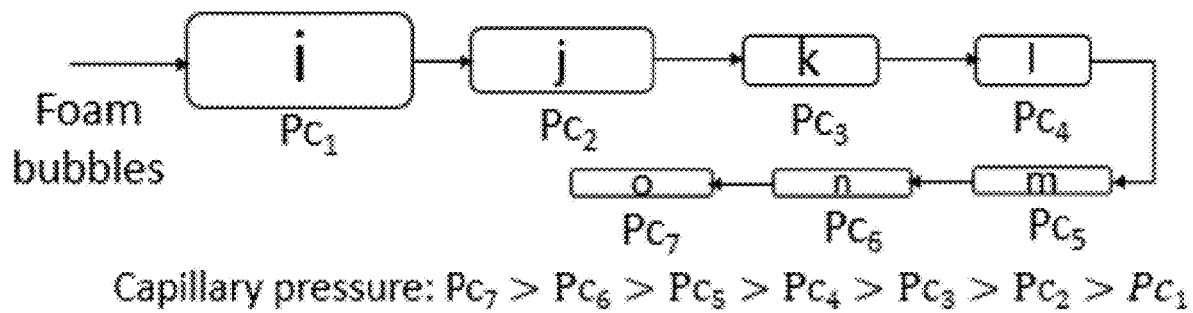
FIG. 5B is a graphical illustration showing a capillary bundle model representing a porous medium.

FIG. 5A is a graphical illustration of foam trapping process in a porous medium showing a magnification of a cross section of the gas saturation profile of sample #1 for four injection cycles. FIG. 5B is a graphical illustration showing a capillary bundle model representing a porous medium. The capillaries are drained (or filled with foams) in series starting from the biggest to the smallest. Different capillaries are filled during each injection cycle.

Referring to FIGS. 5A and 5B (after converting the saturation to gas saturation i.e., $S_g=1-S_w$) illustrates how the different parameters are derived from each cycle. The figures illustrate how the total and trapped foam fraction are directly measured as a function of water saturation from the coreflood experiment. For each cycle of alternate gas and surfactant injection, a fraction of the gas is trapped while a fraction is displaced by surfactant until a local steady state is attained. When no more flowing foam bubble is present, the saturation and pressure drop becomes constant (shown in the figure as the trapped gas saturation, Sgt). Each cycle is also thought to represent a bundle of capillaries. Hence, for every successive cycle of injection, more capillaries are filled with trapped foams. In cycle 1, i number of capillaries (with corresponding capillary pressure $Pc_1$) are filled with trapped foams, and in cycle 2, i+j number of capillaries are filled with trapped foams (with a corresponding capillary pressure, $Pc_2$), and so on until a particular cycle (e.g., cycle 5) in which the maximum number of capillaries (+j+k+l+m) is filled with trapped foams with a corresponding capillary pressure ($Pc_5$). Beyond this cycle (or capillary pressure), no more capillaries can be filled with foam bubbles but only with the wetting phase. Hence, $Pc_5$ is the limiting capillary pressure, Pc*. The flowing or (mobile) foam saturation ($S_{gm}$) for each bundle of capillaries is thus computed as:

$$S_{gm}=S_g-S_{gt} \quad (2)$$

Capillary Pressure and I-R Curves

Some of the measured data set above were used to plot the capillary pressure and I-R curves as shown in FIGS. 6 and 7, respectively. The capillary pressure curve characterizes foam flow in the test sample. Similarly, Initial-Residual (I-R) saturation curve characterizes foam flow in the test sample. The Initial-Residual saturation curve yields a constant (slope of the curve) that is characteristic of the foam and the porous media through which it flows as shown in FIG. 7. The I-R curve can also be fitted with Land's model to obtain a characteristic constant, C, which represents the gas trapping coefficient of the foam and the porous medium (FIG. 7). In-depth graphical analysis of FIG. 4 can be used to derive multiple parameters describing foam flow in a porous medium such as: the amount or fraction of mobile/flowing foam bubbles, the flow rate of the mobile foam, pressure drop required to transport the mobile foam out of a unit length of a rock, and so on.

Figure 8:
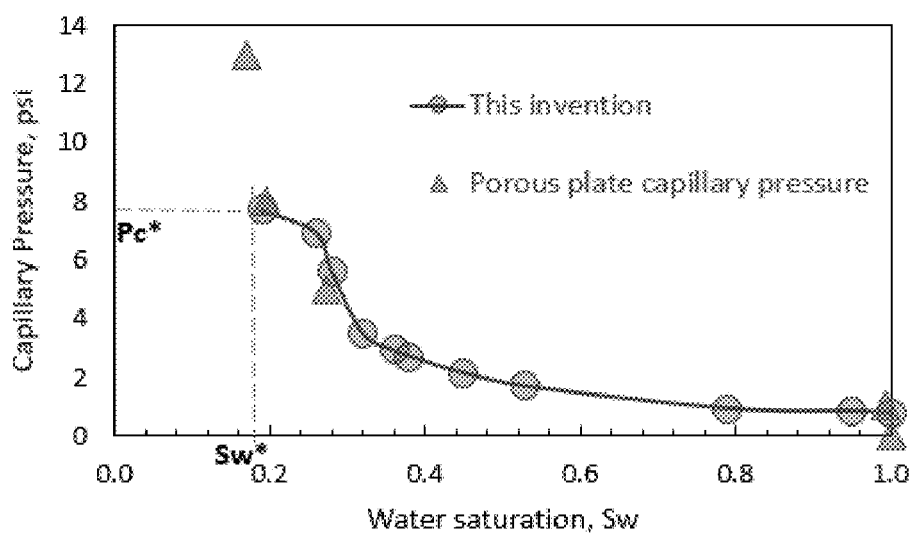
FIG. 8 illustrates a comparison of a porous plate capillary pressure measurement with foam capillary pressure measurement using foam injection in test sample in accordance with the present invention.

In order to validate the accuracy of the methodology in treating a consolidated porous media as a bundle of capillaries of various sizes, the experimental pressure and saturation values in FIGS. 6 and 7 were compared with the capillary pressure measurements obtained from a porous plate capillary pressure method (FIG. 8). As shown in FIG. 8 the pressure-saturation curve in this methodology matches the capillary pressure-saturation curve measured from the porous plate method. Hence, it is correct to use this methodology for the analysis of foam flow distribution and behavior in porous media. In FIG. 6 the maximum pressure of the foam in the test sample is approximately 8 psi with a corresponding water saturation was 0.2. This maximum foam pressure can be related to the limiting capillary pressure of the foam while the water at this pressure can also be related to the critical water saturation of the foam.

The accuracy of this method is dependent on the accurate estimation of water saturation from electrical resistivity measurements. Archie model and other electrical resistivity based water saturation models can be affected by uncertainties in the values of the model parameters. It is preferable to calibrate a chosen model with other in-situ saturation method such as X-ray based saturation. Furthermore, the coreflood experiment is preferably be conducted under a capillary dominated flow so that the pressure drop values at a steady state represent the capillary pressures in the porous medium. This can be achieved with lower injection rates (e.g. 0.01 cm$^3$/min).

While specific embodiments have been described in detail in the foregoing detailed description and illustrated in the accompanying drawings, those with ordinary skill in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. A method for determining capillary pressure and initial-residual (IR) gas saturation curves for a porous rock sample, comprising:
   saturating the rock sample with a surfactant solution to form a saturated rock sample;
   in a first injection cycle:
      injecting a first volume of a gas into the saturated rock sample at a first injection rate, wherein the first volume of the gas is from 0.01 to 0.5 the pore volume of the rock sample; then
      injecting the surfactant solution at the first injection rate into the saturated rock sample and continually measuring at least one of the electrical resistivity or the pressure drop across the rock sample, wherein the surfactant solution is injected until at least one of the electrical resistivity and the pressure drop maintain a constant value; then
   in one or more further injection cycles:
      injecting a second volume of a gas into the saturated rock sample at the first injection rate, wherein the second volume of the gas is from 0.01 to 0.5 the pore volume of the rock sample; then
      injecting the surfactant solution at the first injection rate into the saturated rock sample and continually measuring at least one of the electrical resistivity or the pressure drop across the rock sample, wherein the surfactant solution is injected until at least one of the electrical resistivity and the pressure drop maintain a constant value;
   continuing the further injection cycles until at least one of the electrical resistivity or the pressure drop across the rock sample after an injection cycle is the same as the electrical resistivity or the pressure drop across the rock sample of a preceding injection cycle; and determining at least one of a capillary pressure curve and a water saturation curve based on the plurality of constant values of electrical resistivity and/or pressure drop from the injection cycles.

2. The method of claim 1, wherein the injection cycles are carried out in a single coreflood of the rock sample.

3. The method of claim 2, wherein the pressure drop is measured with a high resolution pressure transducers; and the electrical resistance is measured with an LCR meter.

4. The method of claim 1, further comprising estimating a foam strength and stability in the rock sample.

5. The method of claim 4, wherein the foam stability is above the foam rupture point of the surfactant solution.

6. The method of claim 1, wherein the surfactant solution further comprises one or more nanoparticles.

7. The method of claim 6, wherein the surfactant solution comprises polymer nanoparticles.

8. A coreflooding apparatus for measuring at least one of capillary pressure and initial-residual (IR) gas saturation of a porous media, comprising:
   a hydrostatic core holder, having an inlet port and an outlet port;
   two floating-piston fluid cylinders, wherein one of said floating-piston fluid cylinders contains a surfactant solution while the other floating-piston fluid cylinders contains a gas, and wherein the hydrostatic core holder and said two floating-piston fluid cylinders are disposed inside an oven;
   wherein the inlet port is configured to allow fluids to be injected into one end of a rock sample and to be produced at the outlet port at an opposite end of the rock sample;
   wherein the inlet and outlet ports are connected to pressure transducers, configured to measure a pressure drop across the rock sample;
   an injection pump to displace the fluid from the floating piston cylinders at a constant injection rate;
   a gas dome backpressure regulator configured to provide a back pressure to the rock sample;
   one or more electrode rings imbedded inside a rubber sleeve configured to hold the rock sample in the hydrostatic core holder.

* * * * *